US010722618B2

(12) United States Patent
Hahn et al.

(10) Patent No.: US 10,722,618 B2
(45) Date of Patent: Jul. 28, 2020

(54) APPARATUS FOR CONTROLLING VACUUM DURING OCULAR SURGERY

(71) Applicant: Novartis AG, Basel (CH)

(72) Inventors: Andrew Mason Hahn, Anaheim, CA (US); Andrew David Johnson, Laguna Niguel, CA (US); Brian William McDonell, Irvine, CA (US)

(73) Assignee: Alcon Inc., Rue Louis-d'affry, Fribourg (CH)

( * ) Notice: Subject to any disclaimer, the term of this patent is extended or adjusted under 35 U.S.C. 154(b) by 376 days.

(21) Appl. No.: 15/784,881

(22) Filed: Oct. 16, 2017

(65) Prior Publication Data
US 2018/0104388 A1  Apr. 19, 2018

Related U.S. Application Data

(60) Provisional application No. 62/410,039, filed on Oct. 19, 2016.

(51) Int. Cl.
*A61M 1/00* (2006.01)
*A61F 9/007* (2006.01)

(52) U.S. Cl.
CPC ....... *A61M 1/0031* (2013.01); *A61F 9/00736* (2013.01); *A61M 2205/3344* (2013.01); *A61M 2205/50* (2013.01); *A61M 2205/502* (2013.01); *A61M 2210/0612* (2013.01)

(58) Field of Classification Search
CPC ........ A61M 1/0031; A61M 2205/3344; A61M 2205/50; A61M 2205/502; A61M 2210/0612; A61M 1/0023; A61M 1/0066; A61F 9/00736; A61F 9/007; A61F 9/00781

See application file for complete search history.

(56) References Cited

U.S. PATENT DOCUMENTS

| | | | |
|---|---|---|---|
| 4,395,258 A * | 7/1983 | Wang | A61F 9/00736 604/119 |
| 4,493,698 A | 1/1985 | Wang et al. | |
| 4,770,654 A | 9/1988 | Rogers et al. | |
| 5,342,293 A | 8/1994 | Zanger | |
| 5,429,601 A | 7/1995 | Conley et al. | |
| 5,674,194 A | 10/1997 | Jung | |
| 5,700,240 A | 12/1997 | Barwick, Jr. et al. | |
| 7,524,299 B2 | 4/2009 | Hopkins | |
| 7,811,255 B2 | 10/2010 | Boukhny | |
| 8,287,486 B2 | 10/2012 | Injev | |
| 8,430,840 B2 | 4/2013 | Nazarifar et al. | |
| 8,617,106 B2 | 12/2013 | Zacharias | |

(Continued)

FOREIGN PATENT DOCUMENTS

WO WO2014009111 A1 1/2014
WO WO2014176121 A1 10/2014

*Primary Examiner* — Amber R Stiles

(57) ABSTRACT

A method and system assist a physician in controlling pressure in a line during a surgery. The method includes filtering a vacuum signal such that portions of the vacuum signal having a frequency greater than a threshold frequency (e.g., ten Hz) are not passed. Thus a filtered vacuum signal is provided. The method also includes providing a control signal to a vacuum source. The control signal is selected from the vacuum signal and the filtered vacuum signal. The vacuum source provides a vacuum having a level based on the control signal.

20 Claims, 4 Drawing Sheets

(56) References Cited

U.S. PATENT DOCUMENTS

| | | |
|---|---|---|
| 9,492,318 B2 | 11/2016 | Rockley |
| 9,545,334 B2 | 1/2017 | Steen |
| 9,566,188 B2 | 2/2017 | Raney |
| 9,999,710 B2 | 6/2018 | Ross |
| 10,022,268 B2 | 7/2018 | Peterson |
| 10,219,940 B2 | 3/2019 | Raney |
| 2010/0100075 A1* | 4/2010 | Weston ............... A61M 1/0031 604/543 |
| 2017/0326000 A1 | 11/2017 | Heeren |
| 2017/0333253 A1 | 11/2017 | Heeren |
| 2018/0049920 A1 | 2/2018 | Charles |
| 2018/0104388 A1 | 4/2018 | Hahn |
| 2018/0207032 A1 | 7/2018 | Charles |
| 2018/0207330 A1 | 7/2018 | Ovchinnikov |
| 2019/0350757 A1 | 11/2019 | Charles |

* cited by examiner

APPARATUS FOR CONTROLLING VACUUM DURING OCULAR SURGERY

This application claims the benefit of priority of U.S. Provisional Patent Application Ser. No. 62/410,039 titled "Apparatus for Controlling Vacuum During Ocular Surgery", filed on Oct. 19, 2016, whose inventors are Andrew Mason Hahn, Andrew David Johnson and Brian William McDonell, which is hereby incorporated by reference in its entirety as though fully and completely set forth herein.

BACKGROUND

Ocular surgery frequently involves the removal of fluid and/or tissue from the eye via an aspiration line and replacement of the material removed with fluid provided by an irrigation or infusion line. The aspiration line is coupled to tubing that is connected to a vacuum pump controlled by a console. Similarly, the infusion line is connected to a fluid source via tubing.

During surgery, a cannula connected to the aspiration line is inserted into the patient's eye. To activate the vacuum pump, the surgeon may depress a foot pedal. Pressing the foot pedal through a particular angle causes a vacuum to ramp up to a particular set point. For example, depressing the foot pedal by a particular number of degrees may cause the vacuum pump to provide a vacuum level of −600 mm Hg (millimeters of mercury) (a pressure less than the ambient pressure by 600 mm Hg). This vacuum is applied to the aspiration line in order to remove material from the eye. Fluid may also be provided to the eye via the infusion line to allow the intraocular pressure of the eye to be maintained.

Although the ophthalmic surgery may be performed, patient health may be adversely affected. For example, if the foot pedal is aggressively depressed an amount corresponding to a high vacuum, material may rapidly flow out of the eye. This flow of material may be too fast for fluid from an infusion line to immediately compensate. Consequently, the intraocular pressure may quickly decrease. Eventually, the inflow of fluid from the infusion line returns the intraocular pressure to be within a desired equilibrium range. However, the transient drop in intraocular pressure may still be unsafe for the patient.

Accordingly, what is needed is a mechanism for reducing transient decreases in intraocular pressure.

BRIEF SUMMARY

A method and system to assist a physician in controlling pressure in a line during a surgery. The method includes filtering a vacuum signal such that portions of the vacuum signal having a frequency greater than a threshold frequency (e.g., ten Hz or another selected frequency) are not passed. Thus a filtered vacuum signal is provided. The method also includes providing a control signal to a vacuum source. The control signal is selected from the vacuum signal and the filtered vacuum signal. The vacuum source provides a vacuum having a level based on the control signal.

According to the method and system disclosed herein, the vacuum may be better controlled, reducing or preventing transient drops in intraocular pressure of the patient. Consequently, a physician is better able to prepare for and perform surgery.

DETAILED DESCRIPTION

Figure 1:
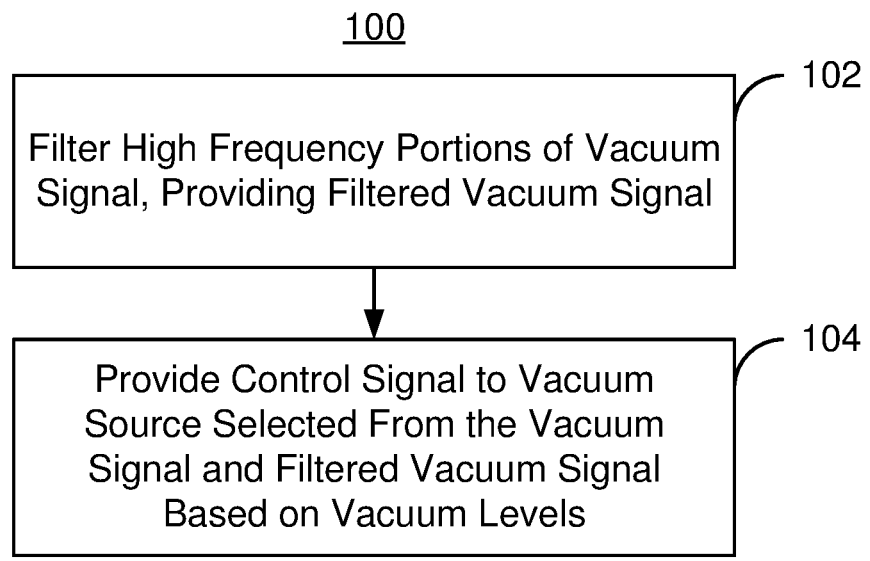
FIG. 1 is a flowchart depicting an exemplary embodiment of a method for assisting a physician in controlling pressure in a line during ophthalmic surgery.

The exemplary embodiments relate to mechanisms for assisting physicians during surgeries including ophthalmic surgery. The following description is presented to enable one of ordinary skill in the art to make and use the claimed embodiments and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the disclosure. Further, although specific blocks are depicted, various functions of the blocks may be separated into different blocks or combined. The exemplary embodiments will also be described in the context of particular methods. However, other methods and/or systems may be implemented (e.g., having different and/or additional parts and parts in different orders than those presented) that are not inconsistent with the exemplary embodiments. Thus, the present disclosure is not intended to be limited to the embodiments shown, but is to be accorded the widest scope consistent with the principles and features described herein. The methods and systems are also described in terms of singular items rather than plural items. One of ordinary skill in the art will recognize that these singular terms encompass plural.

In certain embodiments, the system includes one or more processors and a memory. The one or more processors may be configured to execute instructions stored in the memory to cause and control the process set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Furthermore, aspects of the method and system may take the form of a software component(s) executed on at least one processor and which may be embodied in one or more computer readable medium(s) having computer readable program code embodied thereon.

A method and system assist a physician in controlling pressure in a line during a surgery. The method includes filtering a vacuum signal such that portions of the vacuum signal having a frequency greater than a threshold frequency (e.g., ten Hz) are not passed. Other threshold frequencies are also contemplated (e.g., 0.5 Hz, 1 Hz, 2 Hz, 5 Hz, 15 Hz, 20 Hz, etc.) In some embodiments, the user may set the threshold. In some embodiments, the system may set the threshold based on various criteria (e.g., type of procedure to be performed, user preferences, procedure parameters, etc.) Thus a filtered vacuum signal is provided. The method also includes providing a control signal to a vacuum source. The control signal is selected from the vacuum signal and the filtered vacuum signal. The vacuum source provides a vacuum having a level based on the control signal.

FIG. 1 is a flowchart depicting an exemplary embodiment of a method 100 for assisting a physician during ophthalmic surgery by controlling pressure in a line. For example, the method 100 may be used to control the vacuum in an aspiration line. However, the method 100 may be used to control the vacuum in another line. For simplicity, some parts of the method may be omitted, interleaved, performed in another order and/or combined. The method 100 may include executing instructions on one or more processors or performing operations in hardware. Further, the method 100 is described in the context of ophthalmic, or ocular, surgery. However, the method 100 may be extended to other types of surgery.

Figure 2:
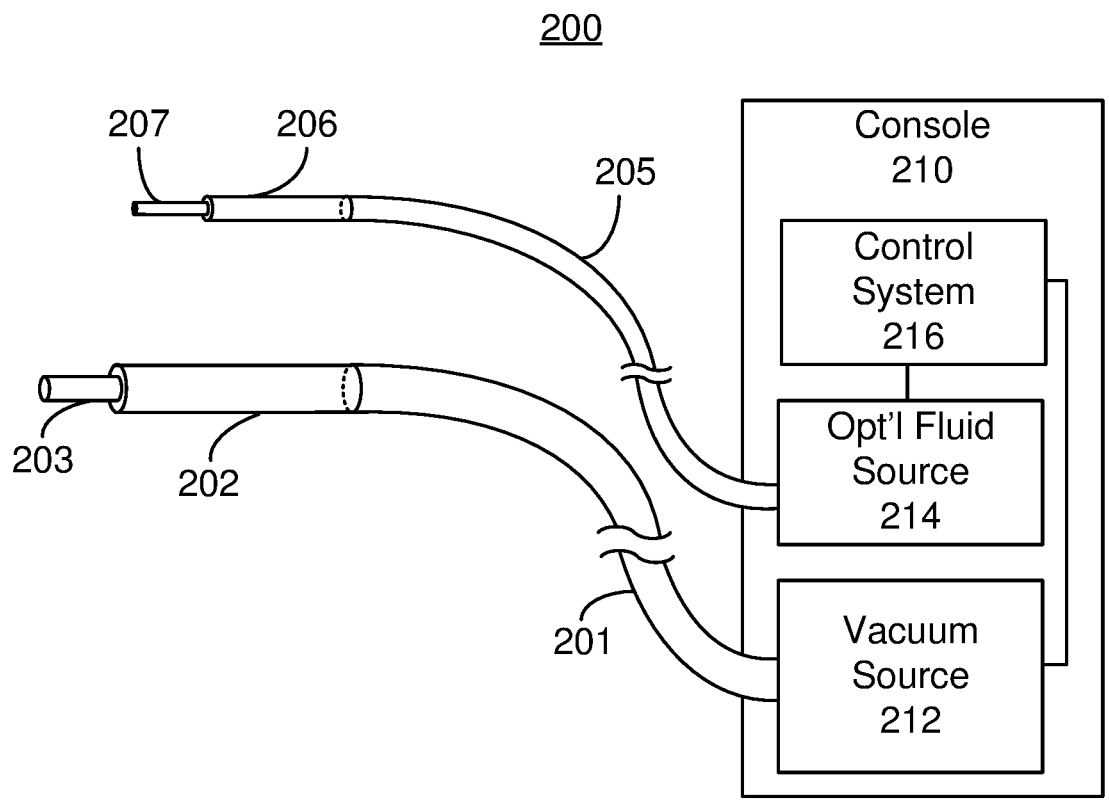
FIG. 2 is a block diagram depicting an exemplary embodiment of an apparatus for controlling vacuum pressure during ocular surgery.

FIG. 2 is a block diagram of an exemplary embodiment of an apparatus 200 for assisting a physician during ocular surgery by controlling pressure in a line. For simplicity, only some components are shown. The components depicted in FIG. 2 may be packaged together in a single apparatus such as the console 210 shown. Alternatively, certain components, such as the vacuum source and/or control system, may be implemented separately. The components may be implemented in hardware and/or software. The apparatus 200 includes a console 210 including a vacuum source 212, an optional fluid source 214 and control system 216. The control system 216 controls the fluid source 214 and the vacuum source 212. The control system 216 may include hardware, a processor executing instructions, or both. The vacuum source 212 may be a vacuum pump such as a peristaltic pump. The fluid source may include a balanced salt solution that can be placed under pressure. Also shown in FIG. 2 are an aspiration line 202 coupled to the vacuum source 212 via tubing 201. A cannula 203 connected to the aspiration line 202 may be inserted into the eye (not shown). Similarly, an irrigation or infusion line 206 is coupled to the fluid source 214 via tubing 205. Another cannula 207 is connected to the infusion line 206 and may be inserted into the eye. However, the console 210 may be used with other lines and/or other surgical instruments.

Referring to FIGS. 1 and 2, the method 100 is described in the context of the system 200 and vice versa. However, one of ordinary skill in the art will recognize that the method 100 could be performed with another apparatus and the system 200 could implement another method. The method 100 commences after a physician or other user has activated the vacuum source 212. For example, the physician or other user may depress a foot pedal that is coupled to the control system 216. Consequently, a vacuum signal may be generated. The vacuum signal may be generated by another component such as a vacuum pedal and provided to the control system 216. Alternatively, the vacuum signal may be generated by the control system 216.

At 102, the vacuum signal is filtered to provide a filtered vacuum signal. The vacuum signal that is filtered at 102 may have been previously processed and/or undergone other filtering. The output vacuum signal differs from the input vacuum signal by the filtering performed at 102. Thus, as used herein, the term vacuum signal and unfiltered vacuum signal merely refer to the vacuum signal prior to filtering in 102.

At 102, the vacuum signal is low pass filtered. Portions of the vacuum signal having a frequency greater than a threshold frequency are removed from the filtered vacuum signal. The threshold frequency may be, for example, ten Hz. In such embodiments, portions of the vacuum signal having a frequency greater than the threshold frequency are not passed. In some embodiments, the threshold frequency may be two Hz. In some embodiments, the threshold frequency may be one Hz. In such embodiments, portions of the vacuum signal having a frequency of greater than one Hz are suppressed. In some embodiments, the threshold frequency is 0.5 Hz. Other threshold frequencies are possible (e.g., 0.1 Hz, 1.5 Hz, 3 Hz, 5 Hz, 15 Hz, 20 Hz, etc.). In some embodiments, at 102, portion(s) of the vacuum signal at the threshold frequency are suppressed. Alternatively, at 102, portion(s) of the vacuum signal at the threshold frequency are passed through. In either case, components having a frequency higher than the threshold frequency are removed. The remaining portion of the vacuum signal is passed to provide the filtered vacuum signal.

The filtering at 102 may be performed using the control system 216. In some cases, the filtering is accomplished by passing the vacuum signal through a low pass filter. The low pass filter may thus be implemented in hardware, in software, or in some combination thereof. The filter may be digital or analog in nature. In some embodiments, an infinite impulse response filter may be used. In other embodiments, a Fourier transform of the vacuum signal may be obtained and the components in frequency space having a frequency exceeding the threshold frequency may be removed. Other and/or additional method(s) of filtering the vacuum signal may be used.

At 104, a control signal based on the filtered and unfiltered vacuum signals is provided to the vacuum source 212. More specifically, the control signal is based on the vacuum levels corresponding to the filtered vacuum signal and the vacuum signal. The control signal determines the level of the vacuum which the vacuum source 212 provides. The control signal may thus determine the set point for the vacuum source 212. As described herein, vacuum is measured in negative pressure, i.e. pressure below atmospheric. For example, a control signal may correspond to a vacuum level of −160 mm Hg, or 160 mm Hg below atmospheric pressure, provided by the vacuum source 212.

At 104, the filtered vacuum signal or the vacuum signal for use in the control signal may be selected depending upon the level of vacuum each signal would cause the vacuum source 212 to provide. At 104, the control system 216 may implement the selection. Further, at 104, a determination may be made as to which of the filtered vacuum signal and the vacuum signal would provide a higher vacuum level and this determined signal may be selected for the control signal. If the filtered vacuum signal and the vacuum signal provide the same level of vacuum, then either one may be selected. For example assume that the filtered vacuum signal would provide a vacuum level of −50 mm Hg, while the vacuum signal would provide a vacuum level of −100 mm Hg. In such a case, at 103, the filtered vacuum signal would be selected as the control signal. Conversely, at 104, if the vacuum signal would provide a vacuum level of −50 mm Hg, while the filtered vacuum signal would provide a vacuum level of −100 mm Hg, the vacuum signal would be selected as the control signal. Consequently, the vacuum source 212 would provide a higher vacuum level and less suction. Alternatively, at 104, the vacuum signal may be filtered to provide the filtered vacuum signal for decreasing vacuum, leave the vacuum signal unchanged for increasing vacuum levels, or, in some embodiments, use a combination of the filtered and unfiltered vacuum signals as the control signal. This may also be seen as selecting between the filtered and unfiltered vacuum signals. At 104, the selection of the filtered vacuum signal or vacuum signal may be repeated throughout activation of the vacuum source 212. The control system 216 may thus dynamically control the vacuum source 212. If the vacuum level is decreasing (more suction provided in the aspiration line 202), this decrease occurs more slowly using the method 100. Alternatively, if the vacuum level is increasing (less suction provided in the aspiration line 202), then this increase occurs quicker than the change in vacuum level while decreasing. During steady state, the vacuum level for the filtered vacuum signal may be the same as the vacuum level for the vacuum signal.

Using the method 100, patient safety may be improved. When a surgeon or other individual increases suction, the method 100 may more slowly change the pressure provided by the vacuum source 212. For example, suppose a user aggressively depresses the vacuum pedal. There are high frequency components to the vacuum signal as it changes in response to this user action. These high frequency components would cause the vacuum level to decrease more rapidly for the vacuum signal. Thus, the vacuum signal would result in lower vacuum levels provided by the vacuum source 212. The filtered vacuum signal does not have these higher frequency components. Consequently, the filtered vacuum signal more slowly decreases the vacuum level. The filtered vacuum signal is, therefore, selected at 104. Because vacuum is decreased more slowly, the intraocular pressure is more likely to equilibrate to changes in the suction provided. Large transient drops in intraocular pressure may thus be reduced or eliminated.

When a surgeon or other individual decreases the suction, for example by releasing the vacuum pedal, the method 100 may select the vacuum signal. There may be high frequency components to the vacuum signal as it changes. The high frequency components cause the vacuum level to increase more rapidly for the vacuum signal. Thus, the vacuum signal would result in higher vacuum levels provided by the vacuum source 212. The filtered vacuum signal does not have these higher frequency components. Consequently, the filtered vacuum signal more slowly increases the vacuum level. As a result, the vacuum signal is selected at 104. Consequently, the vacuum source 212 more quickly increases the pressure provided in a line. This allows a surgeon to rapidly remove suction from tissue or other material that are inadvertently contacted. Damage to the patient's eye may be reduced. Again, patient outcomes may be improved.

Figure 3:
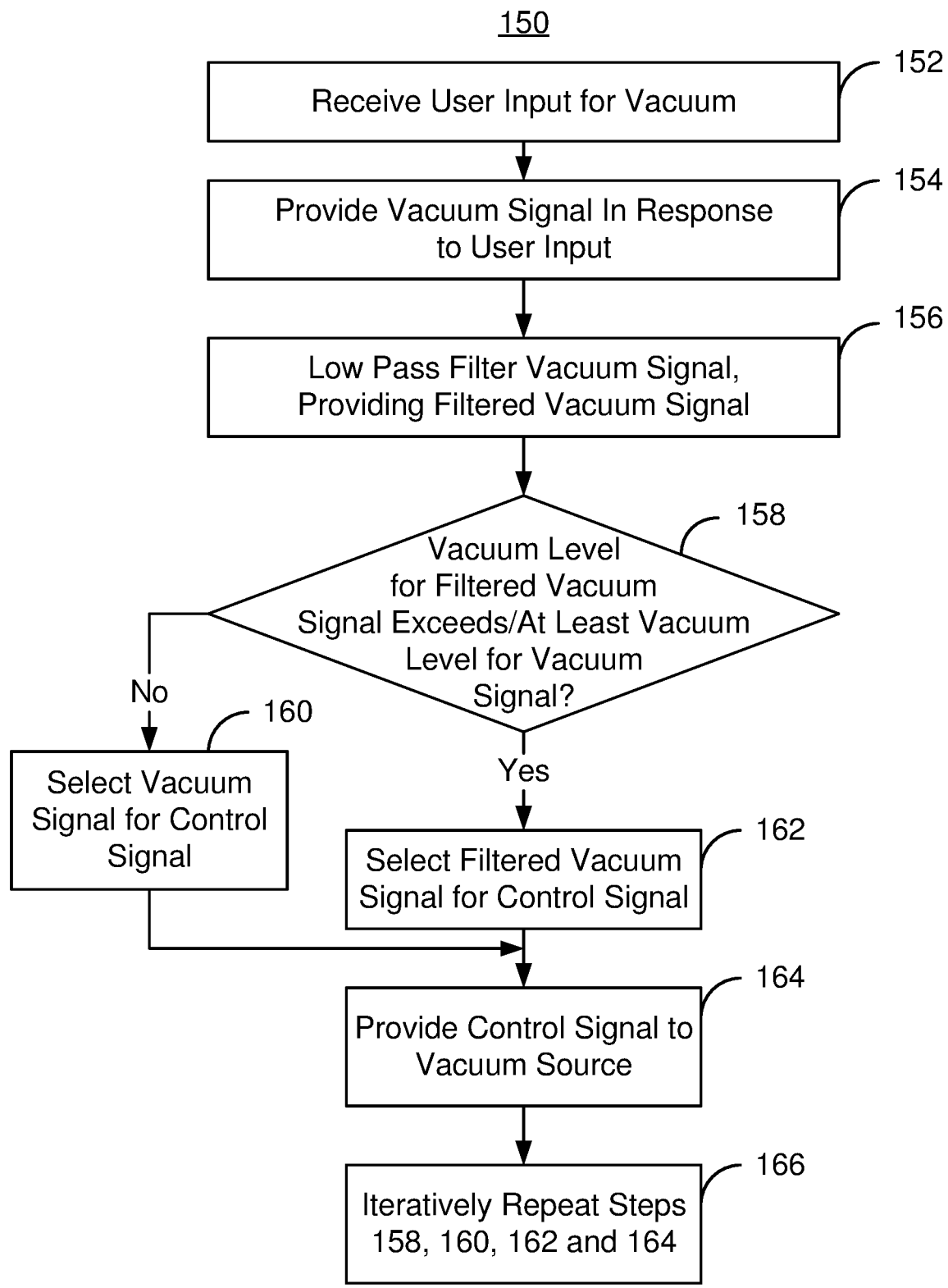
FIG. 3 is a flowchart depicting an exemplary embodiment of a method for assisting a physician in controlling pressure in a line during ophthalmic surgery.

FIG. 3 is a flowchart depicting an exemplary embodiment of a method 150 for assisting a physician during ophthalmic surgery by controlling pressure in a line. For example, the method 150 may be used to control the vacuum in an aspiration line. However, the method 150 may be used to control the vacuum in another line. For simplicity, some parts may be omitted, interleaved, performed in another order and/or combined. The method 150 may include executing instructions on one or more processors or performing operations in hardware. Further, the method 150 is described in the context of ophthalmic, or ocular, surgery. However, the method 150 may be extended to other types of surgery. For simplicity, some parts of the method may be omitted, interleaved, performed in another order and/or combined.

At 152, user input for the vacuum is received. At 152, a signal may be received from a vacuum pedal indicating an amount that the user has depressed the vacuum pedal. In other embodiments, the user input may differ. For example, the user may select a set point for the vacuum level from a menu on a display or undertake an analogous action. The user action thus indicates the desired set point for the vacuum. The set point may be based on how far the vacuum pedal is depressed, how fast the vacuum pedal is depressed, the selection on the menu made by the user or another input. At 154, in response to the user input, a vacuum signal is provided. The vacuum signal may be continued to be provided at 154 throughout use. The vacuum signal indicates the vacuum level desired and generally changes over time.

At 156, the vacuum signal may be low pass filtered to provide a filtered vacuum signal. The vacuum signal that is filtered at 156 may have been previously processed and/or undergone other filtering. The output of 156 differs from the input by the filtering performed at 156. The threshold frequency for the low pass filter may be ten Hz. The threshold frequency may be two Hz in some embodiments. In some embodiments, the threshold frequency may be one Hz. In some such embodiments, the threshold frequency is 0.5 Hz. Other threshold frequencies are possible. Filtering at 156 may thus be analogous to filtering 102. In addition, filtering 156 may be performed as long as the vacuum signal is being provided at 154. For example, the method at 154 and 156 may be performed while the user depresses the vacuum pedal. Once the vacuum pedal is no longer pressed, the method at 154 and 156 may be terminated.

At 158, a determination is made as to whether the level of the vacuum for the filtered vacuum signal exceeds and/or meets the level of the vacuum for the vacuum signal. In some embodiments, the determination may be made as to whether the vacuum level for the filtered vacuum signal exceeds the vacuum level for the vacuum signal. In other embodiments, the determination may be made as to whether the vacuum level for the filtered vacuum signal is at least (greater than or equal to) the vacuum level for the vacuum signal. In some embodiments, the determination is performed by determining whether the filtered vacuum signal meets/exceeds the vacuum signal.

At 160, if the vacuum level for the filtered vacuum signal does not exceed/meet the vacuum level for the vacuum signal, then the vacuum signal is selected as the control signal. At 162, if the vacuum level for the filtered vacuum signal meets/exceeds the vacuum level for the vacuum signal, then the filtered vacuum signal is selected as the control signal. Thus, the signal providing the higher pressure is selected in 160 and 162.

At 164, the control signal is provided to the vacuum source. The vacuum source thus provides the level of vacuum indicated by the control signal. Using the method at 158, 160, 162 and 164 the highest level of vacuum and lowest amount of suction are provided.

At 166, the method at 158, 160, 162 and 164 may be iteratively repeated at particular intervals. Whether the vacuum level for the filtered vacuum signal exceeds/meets the vacuum level for the vacuum signal, selection of the filtered vacuum signal or vacuum signal as the control signal are repeated at a selected time interval. For example, the time interval may be every millisecond, every ten milliseconds, every 100 milliseconds, every time the vacuum signal changes or at other selected interval(s). At 164, the selected signal may continue to be provided to the vacuum source as the control signal throughout the interval. Thus, the vacuum source 212 may be dynamically controlled.

Figure 4:
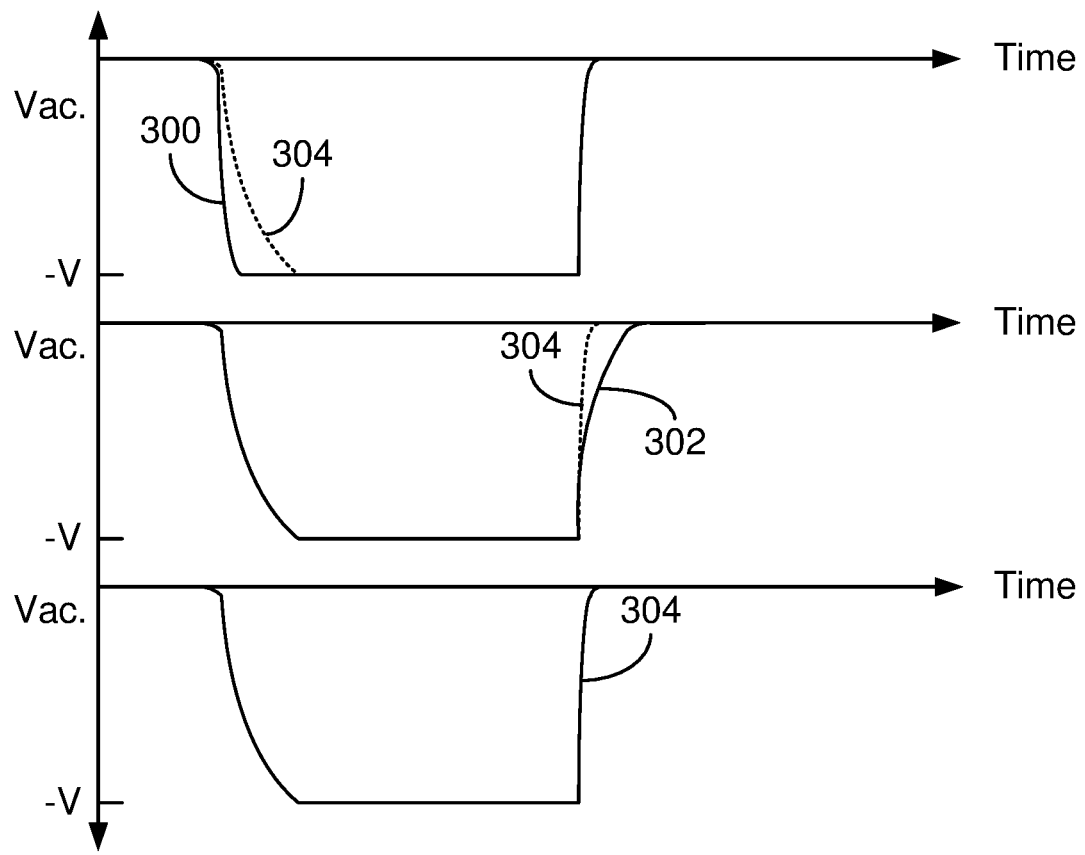
FIG. 4 is a diagram depicting vacuum levels for various control signals.

The method 150 shares the benefits of the method 100. Because the high frequency components of the vacuum signal are removed by filtering and the signal providing the largest vacuum level is selected, large transient changes due to decreases in pressure may be reduced or eliminated. For example, FIG. 4 depicts the vacuum levels for various signals. Shown are vacuum signal level 300 (vacuum level provided by the vacuum signal), the filtered vacuum signal level 302 (vacuum level provided by the filtered vacuum signal) and the control signal level 304 (vacuum level provided by the control signal). For the purposes of explanation, the control vacuum level 304 is depicted in dashed lines along with the vacuum levels 300 and 302. The vacuum levels 300, 302 and 304 are a function of the signals and may be considered to be proportional to the signals in this embodiment. The vacuum signal level 300 decreases rapidly in response to the user depressing the vacuum pedal. Once the set point, −V, is reached, the vacuum signal and thus the vacuum signal level 300 remain constant. Once the user releases the vacuum pedal, the vacuum signal changes rapidly. The vacuum signal level 300 thus increases rapidly. The vacuum signal level 300 rapidly returns to zero (atmospheric pressure). In contrast, the filtered vacuum level 302 responds more slowly because of the low pass filtering of the filtered vacuum signal. Thus, the filtered vacuum level 302 decreases more slowly in response to the user aggressively depressing the vacuum pedal. Note that if the vacuum pedal had been depressed more slowly, the vacuum signal level 300 might be substantially the same as the filtered vacuum level 302. In such a case, the signal selected for the control signal in this interval may not change performance significantly. Once the set point, −V, is reached, the filtered vacuum signal and thus the filtered vacuum 302 remain constant. Once the user releases the vacuum pedal, the filtered vacuum signal changes more slowly. Thus, the filtered vacuum level 302 also increases more slowly. The filtered vacuum level 302 rapidly returns to zero.

As can be seen in FIG. 4, the control vacuum level 304 matches the filtered vacuum level 302 for decreases in pressure and matches vacuum signal level 300 for increases in vacuum level. This is because the filtered vacuum level 302 is higher and responds more slowly for decreases in pressure. In contrast, the vacuum signal level is higher and responds more quickly to increases in pressure. As a result, the control vacuum level 304 matches the vacuum signal level 300 for increasing pressure. As a result, the method 150 may result in slower responses to aggressive requests for increased suction and quicker responses to aggressive requests for decreases in suction. Consequently, transient drops in intraocular pressure may be reduced or eliminated, while errors that might otherwise undesirably remove material from the eye may be more rapidly accounted for. Patient outcomes may thus be improved.

Figure 5:
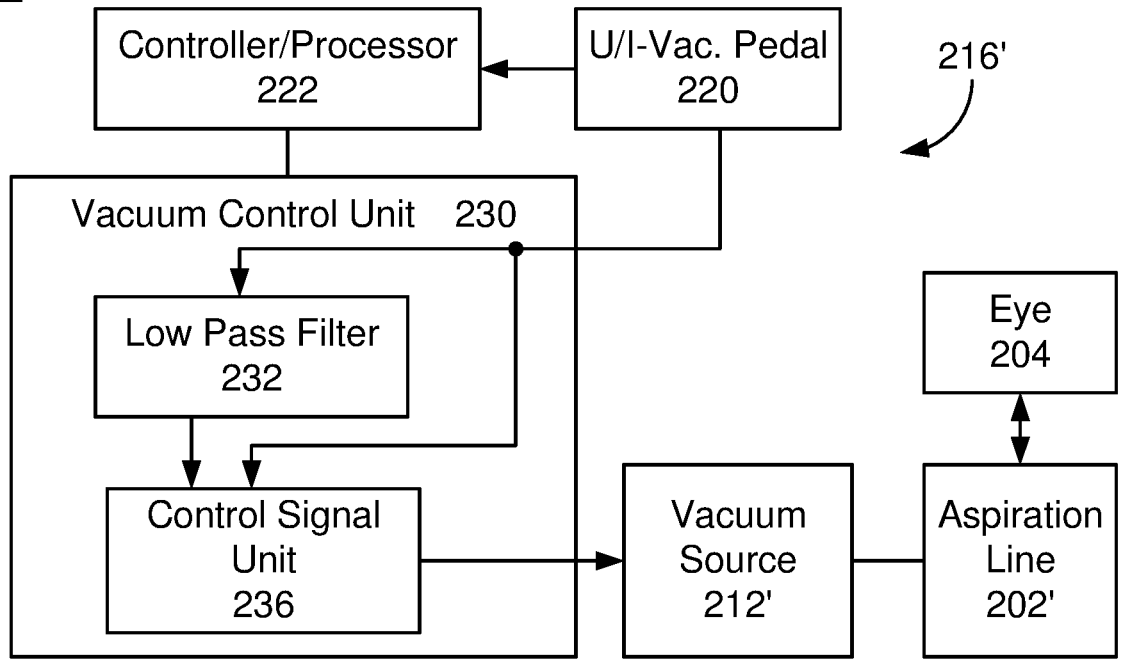
FIG. 5 is a block diagram of another exemplary embodiment of an apparatus for assisting a physician in controlling pressure in a line during ophthalmic surgery.

FIG. 5 is a block diagram of an exemplary embodiment of an apparatus 200' for assisting a physician during ocular surgery by controlling pressure in a line. For simplicity, only some components are shown. The apparatus 200' is analogous to the apparatus 200. Consequently, analogous components have similar labels. The components depicted in FIG. 5 may be packaged together in a single apparatus such as in the console 210 shown in FIG. 2. Alternatively, certain components may be implemented separately. The components may be implemented in hardware and/or software.

The apparatus 200' includes a control system 216' analogous to the control system 216, a vacuum source 212' analogous to the vacuum source 212, and aspiration line 202' analogous to the aspiration line 202. Optional fluid source and other components are not shown and may or may not be included in the system 200'. The control system 216' may include hardware, a processor executing instructions, or both.

The apparatus 200' includes a user interface (U/I) 220, a controller/processor 222, and a vacuum control unit 230. The operator may input instructions and receive output from the U/I 220. The U/I 220 may include a vacuum pedal, a graphical user interface rendered on a display and/or other mechanisms for a user to control vacuum. In the embodiment shown, a vacuum signal is generated by the U/I 220 and provided to the vacuum control unit 230. The method at 152 and 154 may thus be performed via the U/I 220.

The vacuum control unit 230 may be implemented at least in part in software. The vacuum control unit 230 includes a filter unit 232 and a control signal unit 236. The filter unit 232 performs 156 of the method 150. The filter unit 232 may be digital, analog and/or implemented using software. Thus, the filter unit 232 filters the vacuum signal. The vacuum signal and the output of the filter 232 are provided to the control signal unit 236. In some embodiments, a delay is provided between the U/I 220 and the control signal unit 236 in order to synchronize the vacuum signal and the filtered vacuum signal. In other embodiments, any synchronization used may be performed by the control signal unit. The control signal unit 236 performs the method at 158, 160, 162, 164 and 166. Thus, the control signal unit 236 determines whether to use the vacuum signal or the filtered vacuum signal as the control signal. The control signal unit 236 also provides the control signal to the vacuum source 212'. Using the apparatus 300, therefore, the method 100 and/or 150 may be implemented. One or more of the benefits of the methods 100 and/or 150 may thus be achieved.

Figure 6:
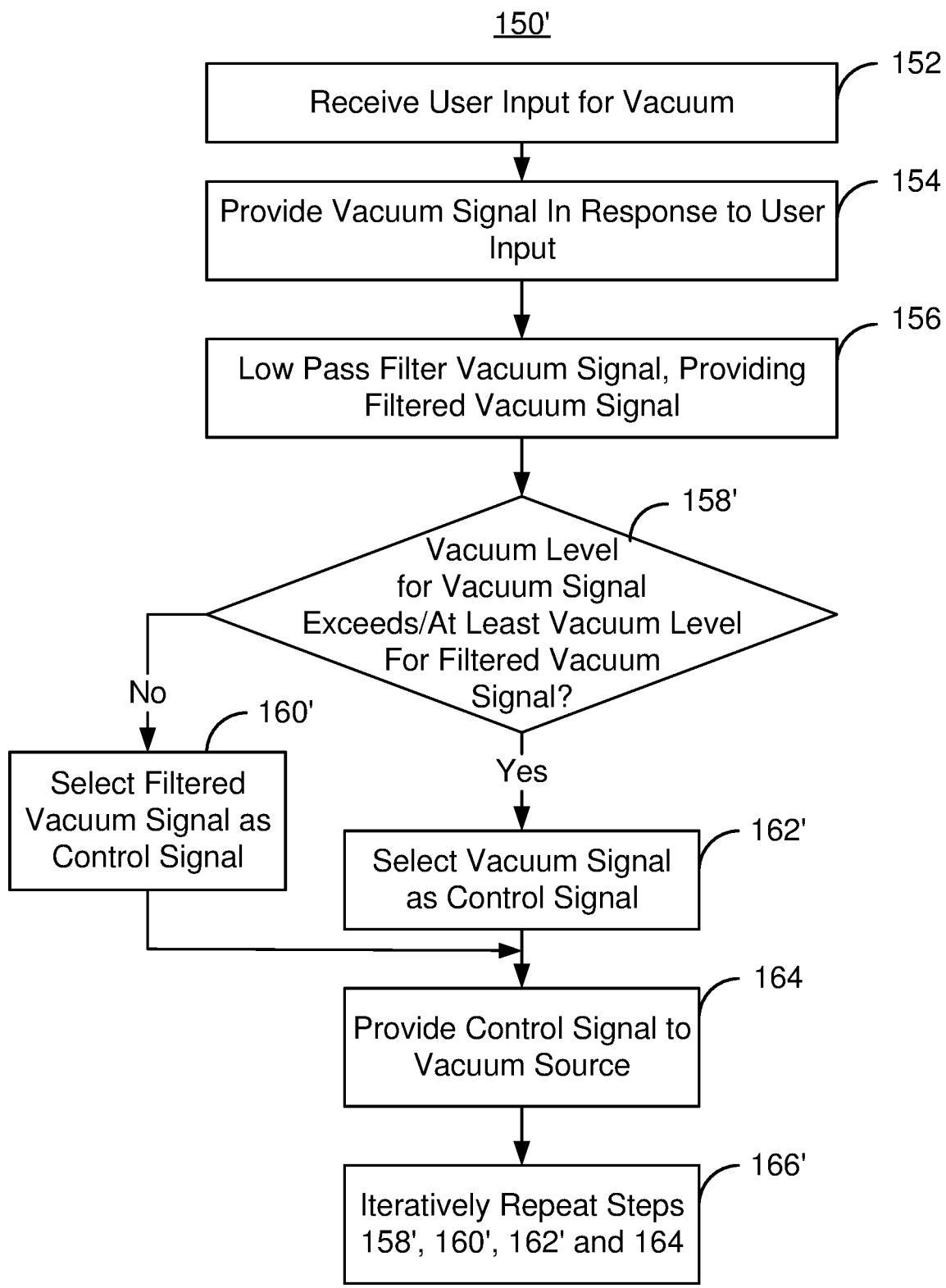
FIG. 6 is a flowchart depicting another exemplary embodiment of a method for assisting a physician in controlling pressure in a line during ophthalmic surgery.

FIG. 6 is a flowchart depicting an exemplary embodiment of a method 150' for assisting a physician during ophthalmic surgery by controlling pressure in a line. For example, the method 150' may be used to control the vacuum in an aspiration line. The method 150' is analogous to the method 150. Consequently, similar parts have analogous labels. Such parts may not be discussed in detail.

The method at 152, 154 and 156 are analogous to those described above for the method 150. Thus, a vacuum signal is provided in response to a user input and filtered such that portions of the vacuum signal above a threshold frequency are suppressed.

At 158', a determination is made as to whether the level of the vacuum for the vacuum signal exceeds and/or meets the level of the vacuum for the filtered vacuum signal. The method at 158' is analogous to but differs from the method at 158.

At 162', if the vacuum level for the vacuum signal does not exceed/meet the vacuum level for the filtered vacuum signal, then the filtered vacuum signal is selected as the control signal, via 160'. If the vacuum level for the vacuum signal meets/exceeds the vacuum level for the filtered vacuum signal, then the vacuum signal is selected as the control signal.

At 164, the control signal is provided to the vacuum source. The method at 164 is thus analogous to 164 of the method 150. The vacuum source thus provides the level of vacuum indicated by the control signal. Using the method at 158', 160', 162' and 164 the highest level of vacuum and lowest amount of suction are provided. At 166', the method at 158, 160, 162 and 164 are iteratively repeated at particular intervals. The method at 166' is analogous to the method at 166. The method 150' shares the benefits of the method(s) 100 and/or 150. Patient outcomes may, therefore, be improved.

A method and system for assisting a surgeon, particularly for ophthalmic surgery, have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. A method for assisting a physician in controlling pressure in a line during a surgery, the method comprising:
    filtering a vacuum signal such that portions of the vacuum signal having a frequency greater than a threshold frequency are not passed, thereby providing a filtered vacuum signal; and
    determining whether a level of a vacuum for the filtered vacuum signal exceeds a level of a vacuum for the vacuum signal;
    providing a control signal to a vacuum source, the control signal being selected from the vacuum signal and the filtered vacuum signal, the vacuum source providing a vacuum having a level based on the control signal;
    wherein providing the control signal further includes selecting the filtered vacuum signal if the level for the filtered vacuum signal exceeds the level for the vacuum signal and selecting the vacuum signal otherwise.

2. The method of claim 1 further comprising:
    repeating the determining the level and selecting the filtered vacuum signal a plurality of times.

3. The method of claim 1 wherein the vacuum signal is provided in response to a user input.

4. The method of claim 1 further comprising:
    determining whether the level of the vacuum for the filtered vacuum signal is at least the level of the vacuum for the vacuum signal; and
    wherein providing the control signal further includes selecting the filtered vacuum signal if the level for the filtered vacuum signal is at least the level for the vacuum signal and selecting the vacuum signal otherwise.

5. The method of claim 1 wherein the threshold frequency is 10 Hz (hertz) or 1 Hz.

6. The method of claim 1, further comprising:
    providing the vacuum signal in response to a user depressing a vacuum control pedal;
    periodically repeating determining whether the level of the vacuum for the filtered vacuum signal exceeds the level of the vacuum for the vacuum signal and providing the control signal to the vacuum source selecting as long as the vacuum control pedal is depressed.

7. A method for assisting a physician in controlling pressure in a line during a surgery, the method comprising:
    filtering a vacuum signal such that portions of the vacuum signal having a frequency greater than a threshold frequency are not passed, thereby providing a filtered vacuum signal; and
    determining whether a level of a vacuum for the vacuum signal exceeds a level of a vacuum for the filter vacuum signal; and
    providing a control signal to a vacuum source, the control signal being selected from the vacuum signal and the filtered vacuum signal, the vacuum source providing a vacuum having a level based on the control signal;
    wherein providing the control signal further includes selecting the vacuum signal if the level for the vacuum signal exceeds the level for the filtered vacuum signal and selecting the filtered vacuum signal otherwise.

8. The method of claim 7 further comprising:
    determining whether the level of the vacuum for the vacuum signal is at least the level of the vacuum for the filtered vacuum signal; and
    wherein providing the control signal further includes selecting the vacuum signal if the level for the vacuum signal is at least the level for the filtered vacuum signal and selecting the filtered vacuum signal otherwise.

9. The method of claim 7, further comprising:
    providing the vacuum signal in response to a user depressing a vacuum control pedal;
    periodically repeating determining whether the level of the vacuum for the vacuum signal exceeds the level of the filtered vacuum for the vacuum signal and providing the control signal to the vacuum source as long as the vacuum control pedal is depressed.

10. The method of claim 7 wherein the threshold frequency is 10 Hz or 1 Hz.

11. An apparatus for assisting a physician in controlling pressure in a line during ocular surgery comprising:
    a filtering unit for receiving a vacuum signal, suppressing portions of the vacuum signal having a frequency greater than a threshold frequency, and providing a filtered vacuum signal including a remaining portion of the vacuum signal; and
    a control signal unit coupled with the filtering unit for providing a control signal to a vacuum source, the control signal being selected from the vacuum signal and the filtered vacuum signal, the vacuum source providing a vacuum having a level based on the control signal;
    wherein the control signal unit further determines whether the level of the vacuum for the filtered vacuum signal exceeds the level of the vacuum for the vacuum signal and selects the filtered vacuum signal if the level for the filtered vacuum signal exceeds the level for the vacuum signal and selecting the vacuum signal otherwise.

12. The apparatus of claim 11 wherein the control signal unit determines the level and selects the filtered vacuum signal a plurality of times.

13. The apparatus of claim 11 wherein the vacuum signal is provided in response to a user input.

14. The apparatus of claim 11 wherein the control signal unit periodically repeats determining the level and selecting the filtered vacuum signal as long as a vacuum control pedal is depressed.

15. The apparatus of claim 11 wherein the filtering unit includes an infinite impulse response filter.

16. The apparatus of claim 11, wherein the control signal unit further determines whether the level of the vacuum for the filtered vacuum signal is at least the level of the vacuum for the vacuum signal and selects the filtered vacuum signal if the level for the filtered vacuum signal is at least the level for the vacuum signal and selecting the vacuum signal otherwise.

17. The apparatus of claim 11 wherein the threshold frequency is 10 Hz or 1 Hz.

18. An apparatus for assisting a physician in controlling pressure in a line during ocular surgery comprising:
- a filtering unit for receiving a vacuum signal, suppressing portions of the vacuum signal having a frequency greater than a threshold frequency, and providing a filtered vacuum signal including a remaining portion of the vacuum signal; and
- a control signal unit coupled with the filtering unit for providing a control signal to a vacuum source, the control signal being selected from the vacuum signal and the filtered vacuum signal, the vacuum source providing a vacuum having a level based on the control signal;

wherein the control signal unit further determines whether the level of the vacuum for the vacuum signal exceeds the level of the vacuum for the filtered vacuum signal and selects the vacuum signal if the level for the vacuum signal exceeds the level for the filtered vacuum signal and selecting the filtered vacuum signal otherwise.

19. The apparatus of claim 18, wherein the control signal unit further determines whether the level of the vacuum for the vacuum signal is at least the level of the vacuum for the filtered vacuum signal and selects the vacuum signal if the level for the vacuum signal is at least the level for the filtered vacuum signal and selecting the filtered vacuum signal otherwise.

20. The apparatus of claim 18 wherein the threshold frequency is 10 Hz or 1 Hz.

\* \* \* \* \*